United States Patent
Hammerer et al.

(10) Patent No.: US 10,376,703 B2
(45) Date of Patent: Aug. 13, 2019

(54) 3D PRINTED CERAMIC TO METAL ASSEMBLIES FOR ELECTRIC FEEDTHROUGHS IN IMPLANTABLE MEDICAL DEVICES

(71) Applicant: MED-EL Elektromedizinische Geraete GmbH, Innsbruck (AT)

(72) Inventors: Dominik Hammerer, Innsbruck (AT); Janika Boltz, Innsbruck (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 65 days.

(21) Appl. No.: 15/158,646

(22) Filed: May 19, 2016

(65) Prior Publication Data

US 2016/0343478 A1 Nov. 24, 2016

Related U.S. Application Data

(60) Provisional application No. 62/164,017, filed on May 20, 2015.

(51) Int. Cl.
*H01B 17/30* (2006.01)
*A61N 1/375* (2006.01)
(Continued)

(52) U.S. Cl.
CPC ............ *A61N 1/3754* (2013.01); *H01B 3/12* (2013.01); *A61N 1/0541* (2013.01); *A61N 1/36036* (2017.08)

(58) Field of Classification Search
CPC ................................ A61N 1/3754; A61F 2/02
See application file for complete search history.

(56) References Cited

U.S. PATENT DOCUMENTS

| 4,678,868 A | 7/1987 | Kraska et al. |
| 5,272,283 A | 12/1993 | Kuzma |

(Continued)

FOREIGN PATENT DOCUMENTS

| EP | 1897588 B1 | 3/2009 |
| WO | WO 2011/025667 A1 | 3/2011 |

OTHER PUBLICATIONS

International Searching Authority, International Search Report—International Application No. PCT/US2016/33166, dated Aug. 23, 2016 together with the Written Opinion of the International Searching Authority, 14 pages.

*Primary Examiner* — Jon Eric C Morales
(74) *Attorney, Agent, or Firm* — Sunstein Kann Murphy & Timbers LLP

(57) ABSTRACT

An electrical feedthrough assembly for an implantable medical device includes an outer ferrule of metallic material having an outer surface hermetically sealed to an implantable device housing. There is an inner feedthrough assembly which is hermetically sealed within the ferrule and which has a structure of sintered layers that include: i. an electrical insulator of ceramic insulator material, ii. one or more electrically conductive vias of metallized conductive material embedded within and extending through the electrical insulator, and iii. a transition interface region around each of the conductive vias comprising a gradient mixture of the ceramic insulator material and the metallized conductive material forming a gradual transition and a mechanical bond between the electrical insulator and the conductive via.

7 Claims, 4 Drawing Sheets

(51) Int. Cl.
  *H01B 3/12*   (2006.01)
  *A61N 1/05*   (2006.01)
  *A61N 1/36*   (2006.01)

(56) References Cited

U.S. PATENT DOCUMENTS

| | | |
|---|---|---|
| 7,164,572 B1 | 1/2007 | Burdon et al. |
| 7,396,265 B2 | 7/2008 | Darley et al. |
| 8,672,667 B2 | 3/2014 | McCusker et al. |
| 8,841,558 B2 | 9/2014 | Morioka et al. |
| 2006/0077638 A1 | 4/2006 | Salmon |
| 2011/0000699 A1 | 1/2011 | Bealka et al. |
| 2011/0106228 A1 | 5/2011 | Reiterer et al. |
| 2011/0186349 A1 | 8/2011 | Troetzschel et al. |
| 2011/0190885 A1 | 8/2011 | Troetzschel et al. |
| 2013/0032378 A1 | 2/2013 | Morioka et al. |
| 2013/0032392 A1 | 2/2013 | Morioka et al. |
| 2014/0008121 A1 | 1/2014 | Troetzschel et al. |
| 2014/0151114 A1 | 6/2014 | Morioka et al. |
| 2014/0161973 A1 | 6/2014 | Tang et al. |
| 2014/0257518 A1* | 9/2014 | McAlpine ............... A61L 27/14 623/24 |

\* cited by examiner ns in vacuum application or for hermetic and insulating sealants in solid oxide fuel cells.
3D PRINTED CERAMIC TO METAL ASSEMBLIES FOR ELECTRIC FEEDTHROUGHS IN IMPLANTABLE MEDICAL DEVICES This application claims priority from U.S. Provisional Patent Application 62/164,017, filed May 20, 2015, which is incorporated herein by reference in its entirety.

FIELD OF THE INVENTION

The present invention relates to implantable medical devices, and more specifically to a hermetically sealed electrical feedthrough for such devices.

BACKGROUND ART

A normal ear transmits sounds as shown in FIG. 1 through the outer ear 101 to the tympanic membrane 102, which moves the bones of the middle ear 103 that vibrate the oval window and round window openings of the cochlea 104. The cochlea 104 is a long narrow duct wound spirally about its axis for approximately two and a half turns. It includes an upper channel known as the scala vestibuli and a lower channel known as the scala tympani, which are connected by a central cochlear duct. The cochlea 104 forms an upright spiraling cone with a center called the modiolar where the spiral ganglion cells of the acoustic nerve 113 reside. In response to received sounds transmitted by the middle ear 103, the fluid-filled cochlea 104 functions as a transducer to generate electric pulses which are transmitted to the cochlear nerve 113, and ultimately to the brain.

Hearing is impaired when there are problems in the ability to transduce external sounds into meaningful action potentials along the neural substrate of the cochlea 104. To improve impaired hearing, auditory prostheses have been developed. When the impairment is associated with the cochlea 104, a cochlear implant with an implanted electrode can electrically stimulate auditory nerve tissue with small currents delivered by multiple electrode contacts distributed along the electrode.

FIG. 1 also shows some components of a typical cochlear implant system where an external microphone provides an audio signal input to an external signal processor 111 in which various signal processing schemes can be implemented. The processed signal is then converted into a digital data format for transmission by external transmitter coil 107 into the implant device 108. Besides receiving the processed audio information, the implant device 108 also performs additional signal processing such as error correction, pulse formation, etc., and produces an electrical stimulation pattern (based on the extracted audio information) that is sent through an electrode lead 109 to an implanted electrode array 110. The electrode array 110 includes multiple electrode contacts 112 on its outer surface that provide selective stimulation of the adjacent neural tissues within the cochlea 104.

The implant device 108 connects to the electrode lead 109 at an electric feedthrough on the outer surface of the implant device 108. The electric feedthrough includes an electrical insulator which contains one or more electrically conductive connectors. The feedthrough is surrounded by an outer ferrule that is hermetically sealed to the housing of the implant device 108. In addition, the electrical insulator and the conductive connectors also must form a hermetical seal within the ferrule to prevent fluids and moisture from entering into the interior of the implant device 108.

To form the required hermetic seal of the electrical feedthrough, the critical issue is the interface between metallic feedthrough ferrule and the ceramic material of the implant device. Ceramics and metals have different material properties which make it difficult to seal the dissimilar materials. Ceramics exhibit an ionic bonding while metals have a metallic bonding that complicates wetting of the ceramic with the metal, which results in poor adhesion of the metal to a ceramic surface. The ceramic and the metal materials also exhibit different thermal expansion coefficients which leads to thermal stress problems.

Various techniques are available to hermetically seal glass/ceramics and metals. For a hermetic glass-to-metal seal, the molten glass must be capable of wetting the metal so that a tight bond is formed. The glass and the metal are strongly bond together when the oxide layer at the metal surface chemically interacts with the glass. In addition, the thermal expansion coefficients of the glass and the metal need to match in order to achieve a stable seal when the assembly cools down. Further hermetic connections can be provided by glass-ceramic-to-metal seals. Glass-ceramics are polycrystalline ceramic materials formed by controlled crystallization in order to adapt the thermal expansion coefficient of the glass-ceramics to the one of metal. Glass-ceramic-to metal seals are in use for electrical feedthroughs in vacuum application or for hermetic and insulating sealants in solid oxide fuel cells.

SUMMARY OF THE INVENTION

Embodiments of the present invention are directed to an electrical feedthrough assembly for an implantable medical device. An outer ferrule of metallic material has an outer surface hermetically sealed to an implantable device housing. There is an inner feedthrough assembly which is hermetically sealed within the ferrule and which has a structure of sintered layers that include: i. an electrical insulator of ceramic insulator material, ii. one or more electrically conductive vias of metallized conductive material embedded within and extending through the electrical insulator, and iii. a transition interface region around each of the conductive vias comprising a gradient mixture of the ceramic insulator material and the metallized conductive material forming a gradual transition and a mechanical bond between the electrical insulator and the conductive via.

In specific embodiments, the electrical insulator may include an insulator outer surface of metallic material adapted for hermetic sealing to the outer ferrule; for example, by sintering or brazing. There may also be one or more electrical circuit components embedded within the electrical insulator. The sintered layers may be based on material deposits made by a 3D printer. For example, the ceramic insulator material may be made of sintered ceramic powder particles.

Embodiments of the present invention also include a cochlear implant device having an electrical feedthrough assembly as described herein.

Embodiments of the present invention also include a method of producing an electrical feedthrough assembly for an implantable medical device. An outer ferrule is provided made of metallic material having an outer surface hermetically sealed to an implantable device housing. An inner feedthrough assembly is produced including: i. providing ceramic insulator material to form an electrical insulator, ii. providing one or more electrically conductive vias of metallized conductive material embedded within and extending through the electrical insulator, and iii. sintering the ceramic insulator material and the one or more electrically conductive layers to form a hermetic boundary that includes a transition interface region around each of the conductive vias comprising a gradient mixture of the ceramic insulator material and the metallized conductive material forming a gradual transition and a mechanical bond between the electrical insulator and the conductive via. The inner feedthrough assembly is located within the outer ferrule, and a hermetic seal is formed between the inner feedthrough assembly and the outer ferrule.

In specific embodiments, the hermetic seal between the inner feedthrough assembly and the outer ferrule may be formed by sintering or brazing. Producing the inner feedthrough assembly also may include embedding one or more electrical circuit components within the electrical insulator. The ceramic insulator material and the one or more electrically conductive vias may be produced by a 3D printing process. The ceramic insulator material may include ceramic powder particles.

Embodiments of the present invention also include a cochlear implant device having an electrical feedthrough assembly produced by a method as described herein.

DETAILED DESCRIPTION OF SPECIFIC EMBODIMENTS

Embodiments of the present invention are directed to an electrical feedthrough assembly for an implantable medical device that is produced by a 3D printing process. The electrical insulator structure and electrically conductive vias embedded within the insulator are printed in a single process, which reduces the number of joining steps. The insulator and the conductive vias are sintered together in combination to provide firmly bonded interlocking between the materials that forms a hermetic seal. And as a result of the printing and sintering processes, the insulating and conducting materials interfuse where they meet across a gradient interface without a clear separation boundary.

3D printing presents an opportunity to create 3-dimensional structures in the bulk material of the electrical insulator that facilitate attachment of conductive members in which it is easy to create different patterns, sizes and geometries of electric contact areas on the opposing sides of the feedthrough component. 3D printing also allows a gradual change in the composition of the electrically conductive vias from oxidation susceptible materials (e.g. niobium, tantalum, etc.) within the bulk insulator material, to less reactive materials (e.g. platinum) at the outer surfaces.

Figure 1:
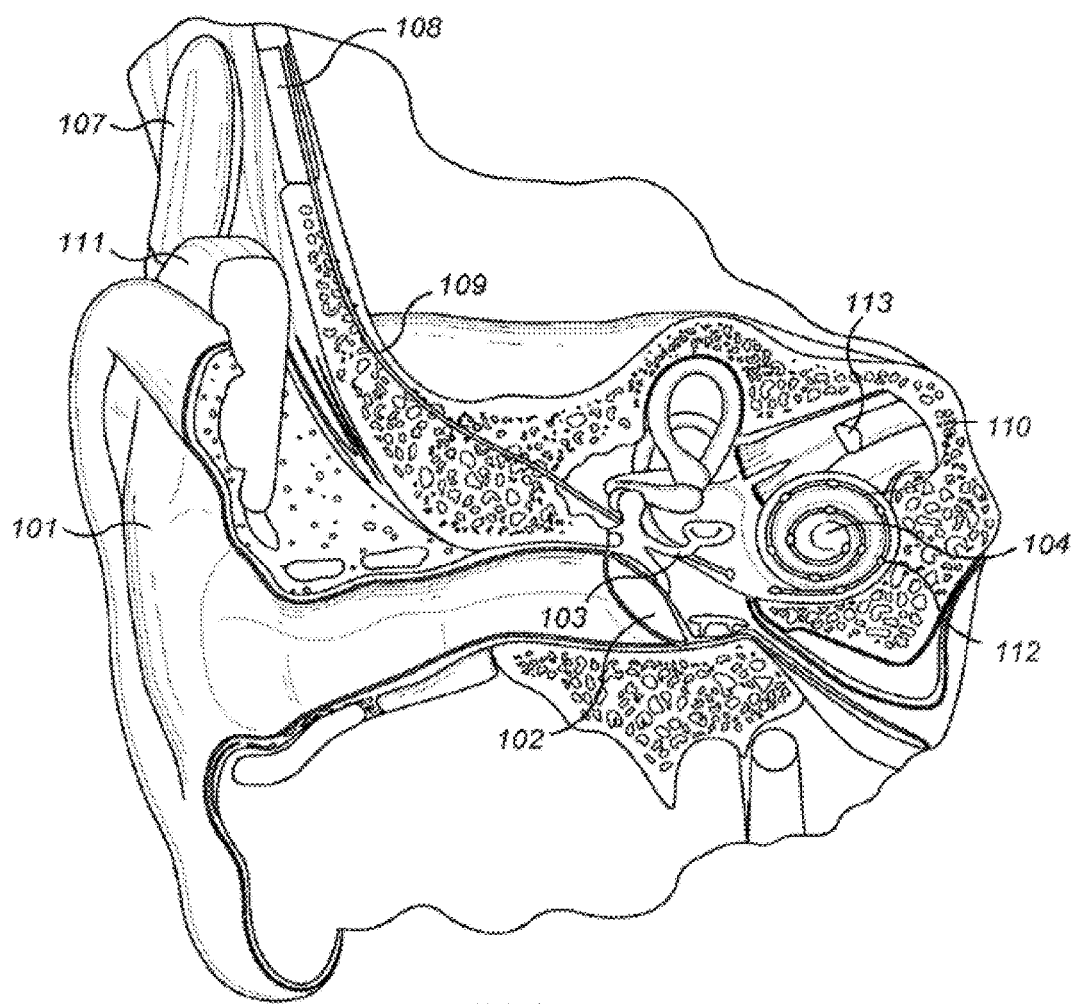
FIG. 1 shows the anatomy of the human ear with a cochlear implant system.
Figure 2:
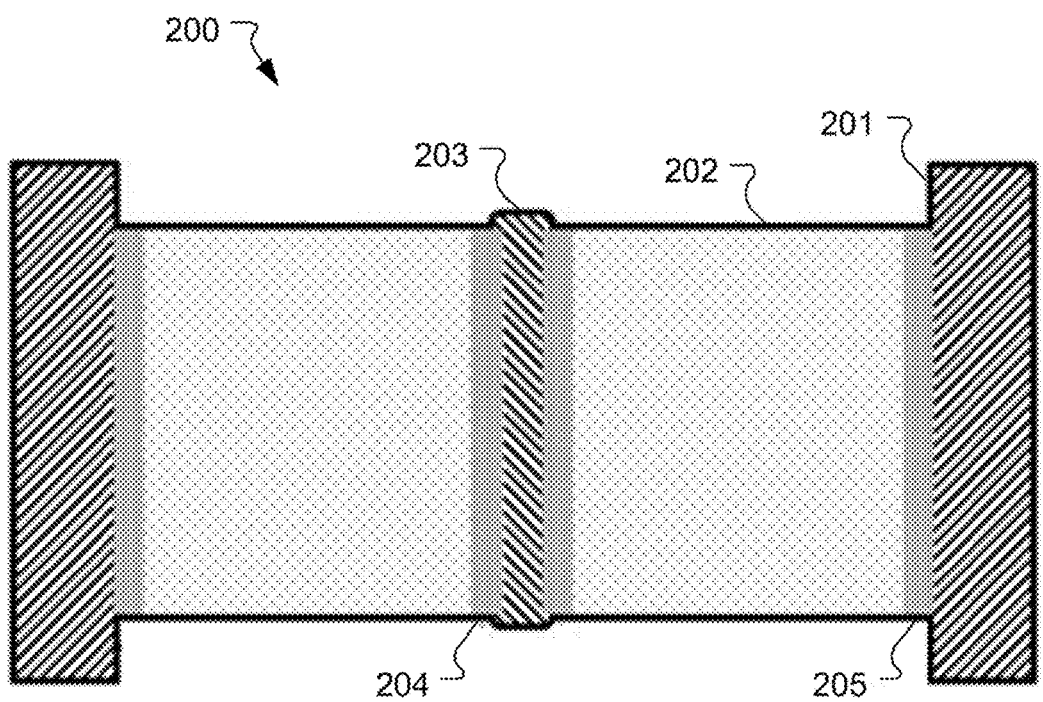
FIG. 2 shows a cross-sectional view of an electrical feedthrough assembly according to an embodiment of the present invention.
Figure 3:
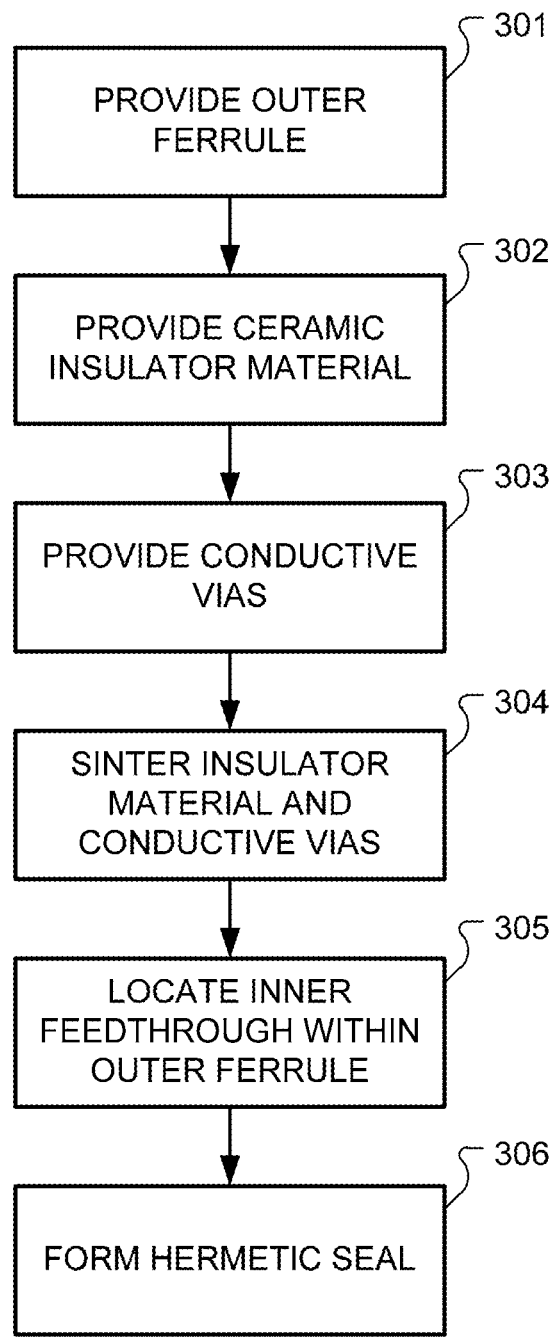
FIG. 3 shows various steps in a method of producing an electrical feedthrough assembly according to an embodiment of the present invention.

FIG. 2 shows a cross-sectional view of an electrical feedthrough assembly 200 according to an embodiment of the present invention, and FIG. 3 shows various steps in a method of producing such an electrical feedthrough assembly 200. The electrical feedthrough assembly 200 provides an outer ferrule 201, step 301, that is made of metallic material. The outer surface of the outer ferrule 201 is hermetically sealed to the housing of an implantable device (not shown).

An inner feedthrough assembly is developed by a 3D printing process that provides one or more layers of ceramic insulator material, step 302, that form an electrical insulator 202, and one or more electrically conductive vias 203, step 303, which are made of metallized conductive material that are embedded within and extend through the electrical insulator 202. The ceramic insulator material of the electrical insulator 202 and the metallized conductive material of the one or more conductive vias 203 are formed by deposits of the material by a 3D printer in a series of layers in a single 3D printing process. The source materials for the electric insulator 202 may typically be a powder bed made of ceramic powder particles provided to a 3D printer as a powder in a fluid environment. For example, ceramics based on $Al_2O_3$ or other biocompatible, oxidic or non-oxidic ceramic materials can be used. The source materials for the electrically conductive vias 203 may typically be dispersions and solutions of metal salts and metal complexes provided to a 3D printer in a fluid environment. These materials may include electrically conductive metal material, electrically conductive ceramics, and electrically conductive oxide materials; for example, platinum, iridium, niobium, tantalum, palladium and their alloys. For example, for a medical application, a palladium alloy may contain silver, copper and/or nickel, such as an alloy of 75% palladium and between 3% and 20% tin, aluminium and/or tantalum, and/or other metallic additives such as niobium, tungsten, molybdenum, zirconium and titanium.

The 3D printer deposits these materials layer by layer in a 3D printing process, steps 302 and 303, that finally forms the 3D printed electrical feedthrough arrangement 200. In the initially printed electrical feedthrough arrangement 200 the source materials of the printed layers still exist in a fluid environment. So there is interfusion between the source material layers of the electrical insulator 202 and the one or more electrically conductive vias 203 so that their respective materials intermingle and diffuse into each other so that the interfaces between them are not clearly separated or sharply defined. Thus, around each of the conductive vias 203 there is a transition interface region 204 that is a gradient mixture of the ceramic insulator material and the metallized conductive material.

In some cases, the materials used to print the electrically conductive vias 203 may include some of the ceramic insulator materials to achieve a predefined resistivity value. Using a mixture of printing materials for the electrically conductive vias 203 may also result in better bonding between the electrical insulator 202 and the one or more electrically conductive vias 203. Controlling a mixture of the printing materials may also be performed to develop gradients in the transition interface region 204 to develop a more conductive region near the electrically conductive via 203, transitioning to a more electrically insulating region near the electrical insulator 202. Such material gradients would also contribute to better bonding between the electrical insulator 202 and the one or more electrically conductive vias 203.

The electrically conductive vias 203 and the electrical insulator 202 may be formed into any desired geometry that can be realized by the additive 3D printing process. For example, the electrically conductive vias 203 may be straight, or in a helical shape to form an inductive coil.

After printing by the 3D printing process, the electrical feedthrough arrangement 200 is then sintered, step 304, to hermetically seal the combination of the electrical insulator 202 and the one or more electrically conductive vias 203. The sintering process avoids formation of a connection by mere compression between the electrical insulator 202 and the one or more electrically conductive vias 203. The sintering also interfuses the materials in the transition interface region 204 to form a gradual transition and a firm mechanical bond between the electrical insulator 202 and the conductive via 203.

The electrical insulator 202 also has an insulator outer surface 205 made of metallic or ceramic/metallic material that is adapted for hermetic sealing to the metallic outer ferrule 201, steps 305 and 306, for example, by sintering or brazing. This metallized interface of the insulator outer surface 205 can be created in the 3D printing process, or by some other conventional technique such as sputter metallization or use of active braze alloys. Besides brazing with pure gold braze, ceramic components can be joined using active brazing alloys, which avoids the need for ceramic metallisation before brazing. The active components of the brazing alloy promote the wetting of the alloy on the ceramic surface. For example, ABA® is a commercially available active brazing alloy of Morgan Technical Ceramics Wesgo Metals (MTC Wesgo). Formation of intermetallic phases that might result from interaction of a pre-braze metallisation layer and braze material can be avoided.

Using a 3D printing process to prepare the electrical feedthrough assembly 200 provides many advantages. The 3D printing process is additive and often applied for rapid prototyping. It provides a flexible way to create different patterns, sizes and geometries of electrical contact locations on opposing sides of the electrical feedthrough assembly 200 to facilitate attachment of conductive members, and also offers the potential to miniaturize the overall size of the electrical feedthrough assembly 200. Printing also reduces the number of processes needed for hermetically sealing the electrical feedthrough assembly 200. The electrical insulator 202 with embedded conductive structures is manufactured in a single manufacturing process and the number of joining steps also is reduced. Moreover, there is no need for handling and assembly of miniature components as is necessary with conventional brazing technology.

Figure 4:
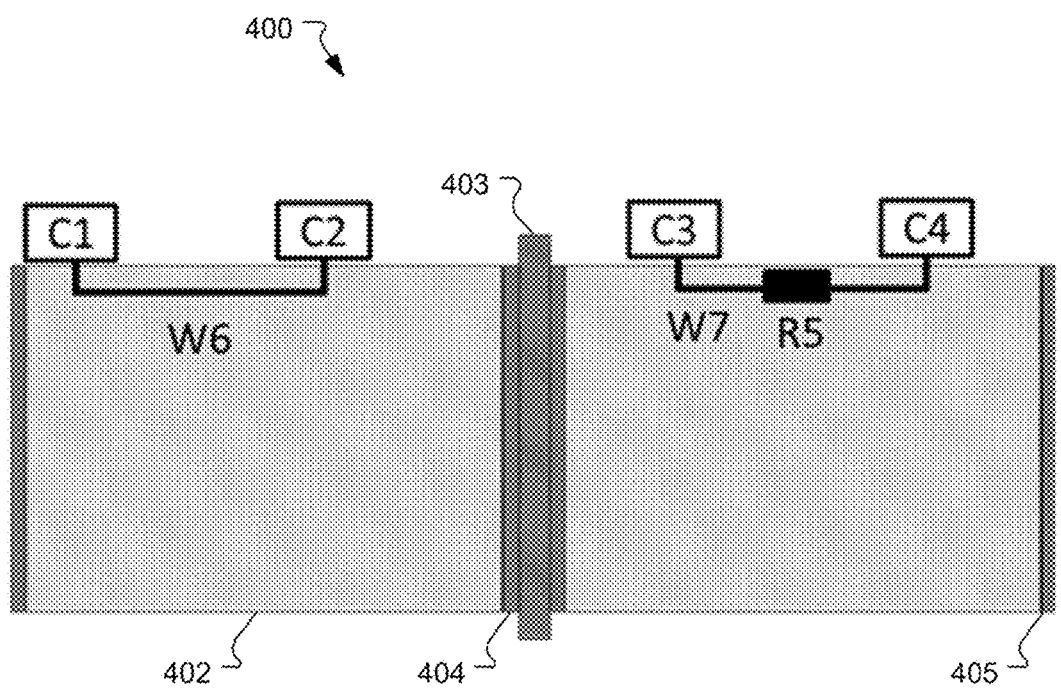
FIG. 4 shows a cross-sectional view of an electrical feedthrough assembly according to another embodiment.

FIG. 4 shows a cross-sectional view of an electrical feedthrough assembly 400 according to another embodiment which includes one or more electrical circuit components embedded within the electrical insulator in addition to or instead of one or more electrically conductive vias 403 with corresponding transition interface regions 404. In such embodiments, the electrical insulator 402 besides having a metallized outer surface 405 for hermetic sealing to an outer ferrule (not shown here) also serves as a substrate for embedded electrical components, like resistors, capacitors, etc., or even entire conductive circuits of multiple such elements. So as shown in FIG. 4, an electrical component C1 may be electrically connected to another electrical component C2 by wire W6. Wire W6 may be made in the same kind of 3D printing process as the electrically conductive vias of FIG. 2. On the right side of FIG. 4, the electric components C3 and C4 are similarly connected via wire W7 and resistor R5. Whereas wire W7 may be made the same way as wire W6, resistor R5 includes more of the electrical insulator material to form a higher ohmic resistance.

In specific embodiments, such electric components and circuits may be located on either or both sides of the electrical insulator 402, and/or they may be embedded within the interior volume of the electrical insulator 402. Even more complicated circuit structures may be realized with the 3D printing process.

Shrinkage of the printing materials during sintering may not be easy to control. And for the 3D printing process, the powder bed and suspensions need to be adapted to avoid formation of cracks upon co-sintering. The 3D printing process is based on powder-metallurgical techniques which lead to porous materials after sintering, and that porosity has to be controlled in order to obtain a hermetically sealed feedthrough assembly. Sintering in combination may need to be performed in a reducing atmosphere to avoid oxidation of the metal, but such a reducing atmosphere may affect the insulating material. Sintering in an oxidizing atmosphere is possible for inert electrically conductive materials used for the electrically conducting vias or the termination of the vias at the surface of the electrical feedthrough assembly.

Although various exemplary embodiments of the invention have been disclosed, it should be apparent to those skilled in the art that various changes and modifications can be made which will achieve some of the advantages of the invention without departing from the true scope of the invention.

What is claimed is:

1. A method of producing an electrical feedthrough assembly for an implantable medical device, the method comprising:
   providing an outer ferrule of metallic material with an outer surface hermetically sealed to an implantable device housing;
   producing an inner feedthrough assembly, the producing including:
   i. providing ceramic insulator material in a fluid environment to form an electrical insulator by a 3D printing process,
   ii. providing metallized conductive material in a fluid environment to form one or more electrically conductive vias by the 3D printing process, the one or more electrically conductive vias embedded within and extending through the electrical insulator, wherein the one or more electrically conductive vias are arranged into a helical shape to form an inductive coil, and
   iii. sintering the ceramic insulator material and the metallized conductive material so as to allow the ceramic insulator material and the metallized conductive material to intermingle and diffuse into each other to form a transition interface region, around each of the one or more conductive vias, that includes a gradual change in composition and a mechanical bond between the electrical insulator and the one or more electrically conductive vias, wherein the sintering is performed in a reducing atmosphere or an oxidizing atmosphere in order to reduce porosity in the inner feedthrough assembly;
   locating the inner feedthrough assembly within the outer ferrule; and
   forming a hermetic seal between the inner feedthrough assembly and the outer ferrule.

2. A method according to claim 1, wherein the hermetic seal between the inner feedthrough assembly and the outer ferrule is formed by sintering.

3. A method according to claim 1, wherein the hermetic seal between the inner feedthrough assembly and the outer ferrule is formed by brazing.

4. A method according to claim 1, wherein producing the inner feedthrough assembly includes embedding one or more electrical circuit components within the electrical insulator.

5. A method according to claim 1, wherein the ceramic insulator material and the one or more electrically conductive vias are produced by a 3D printing process.

6. A method according to claim 5, wherein the ceramic insulator material includes ceramic powder particles.

7. A method according to claim 1, wherein the implantable medical device is a cochlear implant device.

* * * * *